United States Patent [19]

Isaac et al.

[11] 4,218,447
[45] Aug. 19, 1980

[54] ACYL DERIVATIVES OF HELLEBRIGENIN

[75] Inventors: Otto Isaac, Hanau; Klaus Posselt, Bonn; Horst Uthemann, Frankfurt am Main; Klaus Thiemer, Hanau, all of Fed. Rep. of Germany

[73] Assignee: Deutsche Gold- und Silber-Scheideanstalt vormals Roessler, Frankfurt, Fed. Rep. of Germany

[21] Appl. No.: 28,173

[22] Filed: Apr. 9, 1979

Related U.S. Application Data

[63] Continuation-in-part of Ser. No. 858,406, Dec. 7, 1977.

[30] Foreign Application Priority Data

Dec. 17, 1976 [GB] United Kingdom ............... 52759/76

[51] Int. Cl.² ............................................. A61K 31/58
[52] U.S. Cl. .................................. 424/241; 260/239.57
[58] Field of Search ..................... 260/239.57; 424/241

[56] References Cited

U.S. PATENT DOCUMENTS 3,682,891  8/1972  Radscheit et al. .............. 260/239.57

OTHER PUBLICATIONS

Steroids by Fieser et al. (1959), pp. 743 and 784.

Naturwissenschaften, 49, p. 16, Aug. 1962.

Primary Examiner—Elbert L. Roberts
Attorney, Agent, or Firm—Cushman, Darby & Cushman

[57] ABSTRACT

There are prepared compounds corresponding to the general formula:

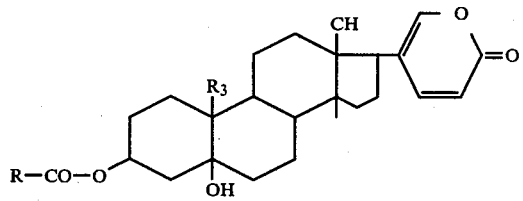

in which R represents a 2,2-dimethylethenyl; isopropyl; nonyl; a $C_3$–$C_6$-cycloalkyl radical; a phenyl group substituted by at least one nitro group, or a $C_1$–$C_6$-alkyl group containing a morpholine group attached thereto, said morpholine ring being substituted zero to twice by $C_1$–$C_6$-alkyl groups; $R_3$ is —CHO or —CH$_2$OH, their optically active forms and their salts. The compounds have cardioactivity e.g., bradycardic effect and have local anethetic, spasmolytic and antiarythmic activity.

13 Claims, No Drawings

ACYL DERIVATIVES OF HELLEBRIGENIN

REFERENCE TO RELATED APPLICATION

This application is a continuation-in-part of application Ser. No. 858,406 filed Dec. 7, 1977. The entire disclosure of the parent application is hereby incorporated by reference and relied upon.

BACKGROUND OF THE INVENTION

This invention relates to new acyl derivatives of hellebrigenin.

Hellebrigenin monoacetate corresponding to the formula

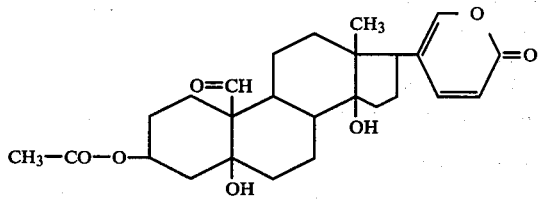

is known. This compound shows a digitalis-like effect when tested in cats (J. Pharmacol. exper. Therapy 99 (1950) 395–400).

SUMMARY OF THE INVENTION

The present invention relates to new hellebrigenin derivatives corresponding to the general formula:

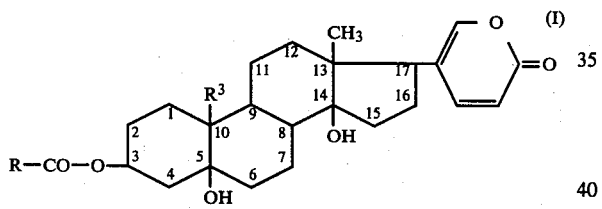

in which R represents a 2,2-dimethylethenyl; isopropyl; nonyl; a $C_3$–$C_6$-cycloalkyl radical; a phenyl group substituted by at least one nitro group, or a $C_1$–$C_6$-alkyl group containing a morpholine group attached thereto, said morpholine ring being substituted zero to twice by $C_1$–$C_6$-alkyl groups; $R_3$ is —CHO or —CH$_2$OH, their optically active forms and their salts. The invention also related to the optically active forms and to the salts of these new hellebrigenin derivatives.

It has surprisingly been found that there does not appear to be any way to predict the resorption quotient for compounds based on R. Thus as shown hereinafter where R is an alkyl or a alkenyl group the resorption quotient varies widely but in no logical manner based on the chain length or branching of the alkyl or alkenyl.

When R is nitro substituted phenyl it normally has 1 to 2 nitro groups, usually two nitro groups, preferably in the 3 and 5 positions.

When R is $C_1$–$C_6$-alkyl morpholino or alkyl substituted morpholino the substituents on the morpholine ring for example can be two methyl group. The morpholino group is preferably in the omega position.

Salts of the compounds which have basic nitrogen atoms can be obtained by reaction with organic or inorganic acids, especially those of the type which are capable of forming therapeutically acceptable salts. Examples of acids such as these are hydrohalic acids, e.g., hydrochloric acid or hydrobromic acid, sulphuric acid, phosphoric acid, phosphorus acid, nitric acid, perchloric acid, organic mono-di- or tri-carboxylic acids of the aliphatic, alicyclic, aromatic or heterocyclic series and also sulphonic acids. Examples of these organic acids are formic acid, acetic acid, propionic acid, succinic acid, glycolic acid, lactic acid, malic acid, tartaric acid, citric acid, ascorbic acid, maleic acid, fumaric acid, hydroxy maleic acid or pyruvic acid; phenyl acetic acid, benzoic acid, p-aminobenzoic acid, anthranilic acid, p-hydroxy benzoic acid, salicylic acid or p-aminosalicylic acid, embonic acid, methane sulphonic acid, ethane sulphonic acid, hydroxy ethane sulphonic acid, ethylene sulphonic acid; halogen benzene sulphonic acids, e.g., p-chlorobenzene sulphonic acid, toluene sulphonic acid, naphthalene sulphonic acid or sulphanilic acid. Salts of the compounds having free carboxyl groups, can be prepared by reaction with inorganic or organic bases, e.g., sodium hydroxide, potassium hydroxide, ammonium hydroxide, calcium hydroxide.

In addition to the compounds set forth in the working examples, other compounds within formula (I) and within the present invention that can be prepared in the same manner as set forth in Table I having the indicated R and $R_3$ groups.

TABLE I

| R | $R_3$ |
| --- | --- |
| cyclopropyl | CHO |
| cyclobutyl | CHO |
| cyclopentyl | CHO |
| morpholinomethyl | CHO |
| morpholinoethyl | CHO |
| morpholinopropyl | CHO |
| morpholinoehexyl | CHO |
| 2,6-dimethylmorpholinoethyl | CHO |
| 2,6-diethylmorpholinomethyl | CHO |
| 2,6-dipropylmorpholinomethyl | CHO |
| 2-methylmorpholinomethyl | CHO |
| isopropyl | CH$_2$OH |
| $CH_3$—C=CH, $CH_3$ | CH$_2$OH |
| nonyl | CH$_2$OH |
| 2,6-dimethylmorpholinomethyl | CH$_2$OH |
| cyclopropyl | CH$_2$OH |
| cyclobutyl | CH$_2$OH |
| cyclopentyl | CH$_2$OH |
| cyclohexyl | CH$_2$OH |
| 3,5-dinitrophenyl | CH$_2$OH |
| 3-nitrophenyl | CH$_2$OH |
| 4-nitrophenyl | CH$_2$OH |
| morpholinomethyl | CH$_2$OH |
| morpholinoethyl | CH$_2$OH |
| 2,4 dinitrophenyl | CH$_2$OH |
| morpholinopropyl | CH$_2$OH |
| morpholinobutyl | CH$_2$OH |
| morpholinohexyl | CH$_2$OH |
| 2,6-dimethylmorpholinoethyl | CH$_2$OH |
| 2,6-diethylmorpholinomethyl | CH$_2$OH |
| 2,6-dipropylmorpholinomethyl | CH$_2$OH |
| 2-methylmorpholinomethyl | CH$_2$OH |

The compounds according to the invention are distinguished by favorable activity. In contrast to the known compound of the J. Pharmacol. exper. Therapy which is not resorbed after oral ingestion, the compounds according to the invention are resorbed to a high degree in the gastrointestinal tract after oral ingestion and have enteral resorption quotients for example of from 30 to 90%. By contrast, the enteral resorption quotient of the known compound is 0. Accordingly, the known compound cannot be orally administered.

By contract, the compounds according to the invention are suitable for oral administration and, hence, for long-term therapy. In particular, the compounds according to the invention have a positive inotropic effect (improvement in the power of contract of the heart), as can be demonstrated for example on the isolated organ (Langendorff's heart, atrium of the heart) or on a complete animal (dog). The Hatcher doses are for example in the extremely favorable range of up to 1 mg/kg and preferably in the range from 0.1 to 0.5 mg/kg. The Hatcher dose is the lowest dose which produces death in cats after 60 to 90 minutes intravenous infusion, and is a standard measure for assessing the activity of powerfully cardioactive compounds.

In addition, the compounds according to the invention have a marked bradycardic effect which is reflected in a reduction in heart rate of up to 30% (in the therapeutic range) and hence results in a normalisation of the increased pulse rate of the damaged heart.

In addition, the abatement levels of the compounds according to the invention in cats are in a therapeutically favourable range, for example, between 20 and 26% in cats. With an abatement level of this order, the active principle is prevented from accumulating to an excessive degree and hence from producing toxic phenomena after repeated administration, which is of particular importance in the case of cardio-active compounds. In addition, the compounds according to the invention are distinguished by negligible side effects. For example, no retching was recorded during infusion in cats. They also show high gastric compatibility (for example no ulcerogenic effect was observed in rats).

The compounds of the invention also have local anesthetic, spasmolylic and antiarrythmic activity.

It is of great significance that the present compounds have no central-nervous activities. Central-nervous activities manifest themselves either as exciting activities (the people concerned are restless, hyperactive, cannot sleep, excited) or as subduing activity (the people are tired, cannot concentrate, cannot drive auto, etc.). An experimental model for testing whether a material has central-nervous activity is the perforated plate test on the mouse according to J. R. Boissier, P. Simon and J. M. Lwoff, Therapie 19 (1964) pages 571, et seg. with which there is tested the increasing or arresting of the orientation mobility.

The compounds of the invention in this test have neither an exciting or an arresting central-nervous activity.

The presently preferred compounds are those of examples 2, 6A, 6B, 10, 11, 12, 13 and 14.

The compounds according to the invention may be produced for example by reacting a compound corresponding to the formula

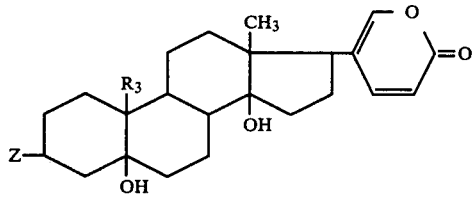 (II)

in which Z is a hydroxy group or a halogen atom, e.g., chlorine or bromine, with an acid corresponding to the formula

R—COOH (III)

in which R is as defined above and of which the carboxyl group may also be activated, and optionally reacting the products of this reaction with morpholine or substituted morpholine. Thus, there can be used the carboxylic acids where R is any of the groups in Table I, supra.

Starting materials of formula (II) where $R_3$ is a —CH$_2$OH group and Z is a hydroxy group are known. Corresponding starting materials where Z is halogen can be made in the customary manner from compounds where Z is a hydroxy group by means of the customary halogenating agents (hydrohalic acids, e.g., hydrochloric acid or hydrobromic acid, thionyl chloride, phosphorus halides, e.g. phosphorus trichloride, phosphorus tribromide or phosphorus pentachloride, sulphuryl chloride, phosphorus oxychloride, phosgene, benzotrichloride).

Compounds of formula (I) wherein $R_3$ is a formyl group can be converted to compounds of formula (I) where $R_3$ is —CH$_2$OH by reducing the formyl group.

In cases where an acid of formula (III) containing an activated carboxyl group is used for the reaction, the compounds in question, where Z is a hydroxy group, are preferably compounds corresponding to the general formula

R—COX in which R is as defined above and X represents a halogen atom, a group of the formula —OR', —SR' or a group of the formula —OSO$_3$H, —O—PO(OH)$_2$, —OP(OR')$_2$, —O—As(OR')$_2$ or —OCO—R" and R' is a C$_1$–C$_6$-alkyl radical or, in the case of —OR' or —SR', also a phenyl radical, a phenyl radical substituted by one or more nitro groups, C$_1$–C$_4$ alkoxy groups, C$_1$–C$_4$-alkyl groups or halogen atoms (chlorine, fluorine, bromine), a cyanomethyl group or a carboxymethyl group, and R" is a linear or branched C$_1$–C$_6$-alkyl group, a C$_1$–C$_6$-alkoxy group, a phenoxy group or a carbobenzoxy group or even the group R. In cases where X is a halogen atom, the halogen atom is preferably chlorine, bromine or iodine; in cases where R' and R" represent alkyl radicals or alkoxy radicals, the radicals in question are preferably of low molecular weight and consist of from 1 to 4 carbon atoms, e.g., methyl, ethyl, propyl, isopropyl, butyl, sec.butyl).

In cases where Z in formula (II) is a halogen atom (chlorine, bromine, iodine), X in formula (IV) is, for example, an alkali metal atom, preferably sodium, potassium or lithium, a silver atom or even —MgCl or —MgBr.

The reaction with a compound of formula (III) or (IV) is carried out for example in a standard solvent or suspending agent such as water, optionally in the presence of a solution promoter (for example lower aliphatic alcohols, e.g., methyl alcohol, ethyl alcohol, isopropyl alcohol, lower aliphatic ketones, e.g., acetone or methyl ethyl ketone, dimethyl formamide) or indifferent agent. Suitable solvents or suspending agents are, for example, low molecular weight aliphatic ethers (for example with 4 to 10 carbon atoms, e.g., diethyl ether, dipropyl ether, diamyl ether); lower molecular weight aliphatic ketones (for example, with 3 to 6 carbon atoms, e.g., acetone, methyl ethyl ketone, ethyl propyl ketone); saturated cyclic ethers, such as tetrahydrofuran, dioxane; low molecular weight saturated chlorinated and fluorinated hydrocarbons with 1 to 5 carbon atoms, the individual C-atoms optionally being substituted once or several times (twice to three times) by chlorine and/or fluorine, such as chloroform, methylene chloride, carbon tetrachloride, perfluoropentane, amyl chloride, 1,2-dichlorethane, 1,1,2-trifluoro-1,2,2-trichloreothane; aromatic hydrocarbons optionally substituted by chlorine or bromine, such as benzene, toluene, xylene, chlorobenzene, bromobenzene, dichlorobenzene, dimethyl formamide, dimethyl sulphoxide, tetramethyl urea, pyridine, N-methyl pyrrolidone. It is of course also possible to use mixtures of the above-mentioned solvents.

The reaction is carried out at a temperature in the range from 0° to 200° C. and preferably at a temperature in the range from 15° to 150° C.

In many cases, especially in cases where X (formula (IV) is a halogen atom or the group —OCOR", the reaction is best carried out in the presence of an acid binding agent, such as alkali metal hydroxides, e.g., sodium hydroxide or potassium hydroxide, alkali metal carbonates, e.g., sodium carbonate or potassium carbonate, alkali metal hydrogen carbonates, e.g., sodium bicarbonate or potassium bicarbonate, trialkyl amines, e.g., triethylamine, dialkyl amines, e.g., dibutyl amine, pyridine and the like or even an excess of compound (II). The acid-binding agent may also be used as solvent either on its own or in admixture with other standard solvents (for example pyridine).

Thus, attention should be paid that the unreacted starting material of formula (IV), particularly if it is an acid chloride, e.g., decanoyl chloride, isobutyryl chloride, is carefully neutralized and removed. Frequently it is recommended that there be a chromatographic purification of the reaction production via silica gel whereby, for example, it is eluted with a chloroform-ethanol mixture (ethanol content, e.g., 1–5%).

In cases where the free acid (formula (III)) is used, it must be activated by the presence of condensation agents such as dicyclohexyl carbodiimide, tetraethyl pyrophosphite, 5-(3'-sulphophenyl)-ethyl iso-oxazole, sulphurous acid-bis-alkylamides (for example SO[N(CH$_3$)$_2$]). N,N'-carbonyl diimidazole and so on (Organic Reactions 12 (1962) 205 and 239).

The reaction component of formula (III) may also be a compound in which one of the groups $R_1$ or $R_2$ is a protective group of the type normally used for amino groups. For example, it is possible to use protective groups normally encountered in the synthesis of peptides and also the methods by which they are normally eliminated. In this connection, reference is made inter alia to the book by Jesse P. Greestein and Milton Winitz entitled "Chemistry of Amino Acids," New York, 1961, John Wiley and Sons, Inc.. Vol. 2, for example, pages 883 et seg. In the end products, protective groups of the type in question may be split off by means of mineral acids, such as hydrochloric acid or sulphuric acid in alcoholic or aqueous-alcoholic solution, or by means of bases, for example, alcoholic alkali liquor (for example methanolic (KOH), at a temperature of from 20° to 100° C. Groups which can be split off by reduction may be eliminated by hydrogenation with hydrogen in the presence of a hydrogenation catalyst (for example palladium, palladium carbon), for example, in ethanol, preferably under normal conditions.

The reduction of compounds of formula (I) wherein $R^3$ is the formyl (—CHO) group to the corresponding compounds where $R_3$ is the —CH$_2$ group takes place in known manner by means of complex metal hydrides (e.g., sodium borohydride, cyanoborohydride, triter, butoxy aluminum hydride) or by means of aluminium alcoholates, according to Meerwein and Ponndorf (e.g., by means of aluminum isopropylate) at temperatures between 0°–150° C., particularly between 20°–100° C. As solvents or suspension agents for this reaction there can be used for example lower aliphatic alcohols, e.g., methyl alcohol, ethyl alcohol or isopropyl alcohol, dioxane, tetrahydrofurane, water or aromatic hydrocarbons such as benzene or toluene or mixtures of these agents.

The compounds which contain asymmetrical carbon atoms and which are generally obtained in the form of racemates may be resolved into the optically active isomers in known manner, for example, by means of an optically active base. It is also possible, however, to use optically active starting materials from the outset, in which case a correspondingly optically active form is obtained as end product.

The compounds according to the invention are suitable for the producton of pharmaceutical compositions and preparations. The pharmaceutical compositions or medicaments contain, as active principle, one or more of the compounds according to the invention, optionally in admixture with other pharmacologically or pharmaceutically active substances, above all with potassium and magnesium aspartate. The medicaments may be prepared with the usual pharmaceutical excipients, assistants, carriers and liluents.

The medicaments may be administered, for example, enternally, parenterally, orally, perlingually or in the form of sprays. They may be made up, for example, in the form of tablets, capsules, pills, dragees, suppositories, liquids or aerosols. Examples of suitable liquids are oily or aqueous solutions or suspensions, emulsions, injectable aqueous or oily solutions or suspensions.

As carriers and assistants, for example, are those recommended in the following literature as adjuvants for pharmacy, cosmetic and related fields such as in Ullmann's Encyklopädie der technischer Chemie, Vol. 4 (1953), pages 1 to 39; Journal of Pharmaceutical Sciences 52 (1963), pages 918 et seq.; N. v. Czetsch-Lindenwald, Hilftstoffe für Pharmazie und angrenzende Gebiete' Phar. Ind. 2 (1961), pages 72 et seq.; Dr. H. P. Fiedler, Lexicon der Hilftstoffe für Pharmazie, Kosmetik und angrenzende Gebiete, Cantor kg. Aulendorf i. Wurtt (1971).

Examples of such materials include gelatin, natural sugars such as sucrose or lactose, lecithin, pectin, starch (for example corn starch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium sterate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil) mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters or saturated and unsaturated fatty acid (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulphoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparation there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerisation generally is between 2 and 40, particularly between 10 and 20.

Such polyoxyethylated materials for example can be obtained by reaction of hydroxyl group containing compounds (for example, mono- or diglycerides or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil, (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metal bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonarily, rectally, nasally, vaginally, linqually, intravenously, intraarterially, intracardially, intramuscularly, intraperitoneally, intracutaneously or subcutaneously.

Because of their good enteral resorption (resorption quota of, for example, 85-90 or even 100%) the compounds of the invention are particularly suited for oral application. The addition of other medicines is also possible.

The compounds of the invention on the isolated guinea pig heart (Langendorff's heart) show a good positive inotropic effect. For example, there is observed in the above-mentioned test methods at a dosage of 3 ug/heart an increase of the strength of contraction of around 20% to 50%.

This positive inotropic activity is comparable to the activity of the known medicine, digitoxin (between 10 and 30 ug).

The lowest clearly positive effective dosage in the above-mentioned animal experiments was for example 0.3 ug/heart (in vitro).

As the general dosage range for the positive inotropic activity (entire animal) there can be used for example 0.05-0.25 mg/kg orally, particularly 0.1 mg/kg; 0.05-0.25 mg/kg intravenously, particularly 0.1 mg/kg.

The compounds of the invention are indicated for use in all degrees and forms of heart insufficiency; aged hearts.

The pharmaceutical preparations generally contain between 0.01 to 5 mg of the active component or components of the invention.

The compounds can be delivered in the form of tablets, capsules, pills, dragees, plugs, salves, gels, creams, powders, dusts, aerosols or in liquid form. As liquid forms there can be used for example oily or alcoholic or aqueous solutions as well as suspensions and emulsions. The preferred forms of use are tablets which contain between 0.2 and 5 mg or solution which contain between 0.001 and 1% of active material.

In individual doses the amount of active component of the invention can be used for example in an amount of:

a. in oral dispensation between 0.01 and 2 mg;
b. in parenteral dispensation (for example intravenously, intramuscularly) between 0.01 to 2 mg.

For example, there is recommended the use of 1 to 3 tablets containing 0.01 and 2 mg of active ingredient 3 times daily or for example, intravenously the injection 1 to 2 times daily of a 0.25 to 5 ml ampoule containing 0.01 to 2 mg of active substance. In oral preparations the minimum daily dosage for example is 0.01 mg; the maximum daily dosage in oral administration should not be over 5 grams.

In veterinary medicine the compounds of the invention can be used in treating dogs and cats. The individual dosages in general are between approximately 0.002 and 1 mg/kg body weight.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 5 mg/kg and 500 mg/kg, in some cases even above 1000 mg/kg.

The drugs can be used in human medicine, in veterinary medicine as well as in agriculture alone or in admixture with other pharmacologically active materials.

Unless otherwise indicated all parts and percentages are by weight.

The compositions can comprise, consist essentially of or consist of the materials set forth.

The following examples include the preparation of some of the comparison compounds as well as preparation of compounds within the invention.

DESCRIPTION OF THE PREFERRED EMBODIMENTS AND COMPARISON COMPOUNDS

EXAMPLE 1

Hellebrigenin-3-$\beta$-butyrate 2.08 of hellebrigenin (0.005 mole) were dissolved in 20 ml of pyridine and 15 ml of n-butyric acid anhydride were added to the resulting solution. The mixture was left standing for 60 hours, after which 300 ml of diethyl ether were added. On standing overnight in a refrigerator, crystals were precipitated and were filtered off under suction, washed with ether and dried. The product obtained was chromatographed on silica gel and recrystallised from 50% aqueous ethanol. 1.2 g of white needles were obtained. M.P.: 212° C.

EXAMPLE 2

Hellebrigenin-3$\beta$-isobutyrate 2.08 g (0.005 mole) of hellebrigenin were dissolved in 20 ml of pyridine and 10 ml of isobutyric acid anhydride were added to the resulting solution. After 24 hours, 400 ml of diethyl ether were added, after which the mixture was left standing overnight in a refrigerator to crystallize out. The substance was purified by column chromatography on silica gel and was recrystallised from 50% aqueous ethanol.

EXAMPLE 3

3$\beta$-Isovaleric acid ester of hellebrigenin 2.08 g (0.005 mole) of hellebrigenin and 10 ml of isovaleric acid anhydride were heated for 1 hour to boiling point in 20 ml of pyridine. After cooling, 400 ml of diethyl ether were added. On standing in a refrigerator, a crude product crystallises out and was purified by column chromatography, followed by recrystallisation from 50% aqueous ethanol. Yield: 1.5 g; M.P.: 196°–199° C. (*

*The symbol "3$\beta$" before the name of the acid indicates that the hydroxy group in the 3$\beta$-position of the hellebrigenin is attached to the acid radical. This also applies to all the following Examples.)

EXAMPLE 4

Hellebrigenin-3$\beta$-(3,3-dimethyl-butyrate)

2.8 g (0.0067 mole) of hellebrigenin and 15 ml of 3,3-dimethyl butyric acid chloride were boiled under reflux for 2 hours in 60 ml of methylene chloride. The reaction solution was then washed three times with water and three times with saturated sodium bicarbonate solution, dried over magnesium sulphate and the solvent distilled off. Diethyl ether was added to the residue which was then left standing overnight, as a result of which the reaction product (crude product) crystallised. It was recrystallised from 120 ml of methanol. Yield: 1.8 g; M.P.: 237° C.

EXAMPLE 5

3$\beta$-Crotonic acid ester of hellibrigenin 6.8 g (0.0163 mole) of hellebrigenin were boiled under reflux for 1 hour in 210 ml of chloroform and 6 ml of crotonic acid chloride. The reaction mixture was worked up in the same way as in Example 4. The reaction product was recrystallised twice from methanol. Yield: 0.8 g; M.P.: 202°–204° C.

EXAMPLE 6A

3$\beta$-(3,3-Dimethylacrylic acid ester) of hellebrigenin 5 g (0.012 mole) of hellebrigenin were boiled under reflux for 2 hours in 100 ml of methylene chloride and 5 ml of 3,3-dimethyl acryloyl chloride. The reaction mixture was worked up in the same way as in Example 4. The reaction product obtained (4 g) was dissolved in 40 ml of boiling ethanol. The impure product which had crystallised out was discarded. The ethanolic mother liquor was distilled off and the residue was treated with ether, giving 1.2 g of the title substance which was recrystallised from 16 ml of methanol. Yield: 0.7 g; M.P.: 194°–196° C.

EXAMPLE 6B

3$\beta$-(3,3-Dimethylacrylic acid ester) of hellebrigenin

The procedure of Example 6B is a better procedure for producing the same product as in Example 6A.

20 g (0.048 mole) of hellebrigenin under a nitrogen flow were suspended in 400 ml of dry methylene dichloride. There were added 20 ml=20 g (0.148 mole) of freshly distilled 3,3-dimethyl acryloyl chloride and the mixture heated at reflux for 1.5 hours; attention is paid thereto to excluding moisture. The hellebrigenin dissolved. The mixture was allowed to cool and to destroy the excess acid chloride. There were added 20 ml of absolute methanol. There occurred a strong evolution of hydrochloric acid, to completely destroy the residual acid chloride the mixture was boiled at reflux for a further 30 minutes.

The cooled reaction was shaken in a separatory funnel with 100 ml of water, then three times, each time with 100 ml of saturated $NaHCO_3$ solution, and again with 100 ml of water; the methylene chloride solution was dried with anhydrous sodium sulphate and concentrated in a vacuum. The yellow oil formed was taken up with 50 ml of dry chloroform and stirred in 1500 ml of benzine (B.P. 50°–70° C.) whereupon the reaction product precipitated out (24.8 g). The further purification was carried out by column chromatography on silica gel (Geduran S 100, 0.063–0.200 mesh) at 20° C.

The crude product was taken up in 50 ml chloroform/ethanol (98% chloroform, 2% ethanol) and passed to a 132 cm long column (inner diameter 6 cm). The eluation was carried out with the same liquid mixture. Extensive protection against light was provided by a brown colored cooling jacket and the temperature held constant at 20° C. The rate of flow was 115 ml/minute. The individual components were collected separately. As soon as the desired main product comes, the process can be shortened by increase of polarity.

The main fraction was concentrated in a vacuum almost to dryness, then taken up with 50 ml of $CHCl_3$ and precipitated with 1.5 liters of benzine (B.P. 50°–70° C.), filtered off with suction and dried in a vacuum at 50° C. Yield: 15 g=62.6%; M.P.: 194°–196° C.

The procedure set forth in Example 6B for working up the reaction mixture can also be used in working up the reaction mixture in those examples which refer to working up in the same way as in Example 4.

EXAMPLE 7

3β-Caprylic acid ester of hellebrigenin 2.08 g (0.005 mole) of hellebrigenin were heated under reflux for 2 hours in 20 ml of pyridine and 10 ml of caprylic acid anhydride. The crude product was precipitated with diethyl ether, chromatographed on a column of silica gel and recrystallised from 50% aqueous ethanol. Yield: 1.1 g; M.P.: 189°–191° C.

EXAMPLE 8

3β-Decanoic acid ester of hellebrigenin 2.08 (0.005 mole) of hellebrigenin were boiled under reflux for 3 hours in 20 ml of pyridine and 10 ml of decanoic acid anhydride. After cooling, the crude product was precipitated by the addition of 500 ml of water, chromatographed on a column of silica gel and recrystallised from 66% aqueous ethanol. Yield 1.6 g; M.P. 188° C.

EXAMPLE 9

Hellebrigenin-3β-(3,5-dinitrobenzoate)

2.08 g (0.005 mole) of hellebrigenin were boiled under reflux for 8 hours in 20 ml of pyridine and 5 g of 3,5-dinitrobenzyl chloride. The reaction product was precipitated with water, chromatographed on silica gel, dissolved in chloroform and precipitated with petroleum ether. Yield: 0.5 g; M.P. 172° C.

EXAMPLE 10

Hellebrigenin-3β-(2,6-dimethylmorpholinoacetate)

2.5 g (0.005 mole) of 3-chloroacetyl hellebrigenin were heated under reflux for 2 hours in 25 ml of acetone and 5 ml of 2,6-dimethyl morpholine. The solvent was distilled off and the residue was stirred for 1 hour with 200 ml of water. 2 g of the title-substance (base) were obtained, melting at 196°–198° C. after recrystallisation from isopropanol.

Production of the hydrochloride:

2 g of the base melting at 196°–198° C. were dissolved in 20 ml of acetone, neutralised with isopropanolic hydrochloric acid, the hydrochloride 92 g) was precipitated by the addition of 30 ml of diethyl ether and recrystallised from 30 ml of ethanol. Yield: 1 g; M.P.: of the hydrochloride 178°–180° C. (hygroscopic).

EXAMPLE 11

3β-Cycloporpane carboxylic acid ester of hellebrigenin 800 mg of hellebrigenin were suspended in 50 ml of $CH_2Cl_2$ and there was added 1 g of cyclopropane carboxylic acid chloride and the mixture boiled for 4 hours at reflux. Working up and purified by column chromatography in the manner described in Example 4. Yield: 500 mk; M.P. 140°/240° C.

EXAMPLE 12

Hellebrigenol-3β-isobutyrate 1.5 grams (0.0031 mole) of hellebrigenin-3β-isobutyrate were dissolved in 60 ml of absolute tetrahydrofuran and treated at room temperature with 60 ml of freshly prepared reduction solution of lithium-tri-tert.-butoxy-aluminium hydride in tetrahydrofurane (produced from 1.5 grams of $Li(AlH_4)$ and 6 grams of tert. butanol). After stirring for two days at room temperature the reaction mixture was heated with 5% acetic acid and shaken with chloroform. The solution obtained was concentrated, the reaction product precipitated by the addition of petroleum ether and purified by column chromatography on silica gel (elution agent chloroform 95 volume %/ethanol 5 volume%). Yield: 30% M.P. 195° C.

EXAMPLE 13

Hellebrigenol-3β-(3,3-dimethyl-acrylate)

1 gram (0.002 mole) of hellebrigenin-3β-(3,3-dimethyl-acrylate) was dissolved in 60 ml of absolute tetrahydrofurane and treated at room temperature with 60 ml of a freshly prepared reduction solution of lithium tri-tert.-butoxy-aluminium hydride (made as in Example 16). After one hour reaction time the mixture was treated with 5% acetic acid and extracted several times with chloroform. The solution was concentrated and the reaction product precipitated by the addition of petroleum ether. Yield: 49.8%. M.P. 140° to 142° C.

EXAMPLE 14

3-β-Cyclohexanecarboxylic acid ester of hellebrigenin 2 grams of hellebrigenin and 4 ml of cyclohexanecarboxylic acid chloride were reacted in a manner analogeous to Example 11 (without column chromatographic purification). Yield: 90%, M.P. 211° to 214° C. (decomposition).

Example of pharmaceutical formulations of the compound of Example 2 are given below:

Injection solution 2 mg of the compound of Example 1 in the form of the hydrochloride salt are dissolved in 200 mg of propylene glycol and the solution filled up with water to a total volume of 2 ml. After filtration, the solution is filled into ampoules.

| Tablets: | |
|---|---|
| A 150 mg tablet contained | |
| Compound of Example 2 | 5.0 mg |
| Lactose | 124.1 mg |
| Polyvinylpyrrolidone | 5.0 mg |
| Cornstarch | 15.0 mg |
| Highly dispersed silica | 0.5 mg |
| Magnesium stearate | 0.4 mg |

The compounds of Example 2 is mixed with the lactose and cornstarch and moistened with a solution of polyvinyl pyrrolidone in water; the composition is thoroughly worked, dried, sieved and after addition of the highly dispersed silica and magnesium stearate pressed into tablets.

Example of pharmaceutical formulations of the compound of Example 6 are given below:

Tablets (1) 63 g of 3β-(3,3-Dimethylacrylic acid ester) of hellebrigenin were dissolved with stirring in 7 kg ethanol
 =Solution 1
(2) 1.06 kg of cornstarch were caused to swell in 15 kg demineralized water with warming
 =Starch paste
(3) Solution 1 was mixed with the starch paste with stirring
 =Granulating slime
(4) 88.087 kg of Lactose were intensively mixed with the granulating slime. After that the wet mixture was passed through an Alexanderwerk Granulating machine having a screen with a width of mesh of 2 mm. The resulting granulate was dried in a warm air drying cabinet at 50° C.
 =Dried granulate
(5) The dried granulate was then homogenously mixed in a mixer (Turbula mixer) with 10.0 kg of cornstarch, 0.6 kg of highly dispersed silica (Aerosil 200 V) and 0.25 kg of Magnesium stearate
 =Pressing composition
Relative humidity: 35±5% sina equi Hygro scope.
(6) From this pressing composition there were produce tablets.

| | |
|---|---|
| Tablet weight | : 100 mg |
| Tablet measurements | |
| Diameter | : 6 mm |
| Surface | : concave |
| Radius of curvatures | : 6 mm |
| Thickness | : 3.2 ± 0.1 mm |
| Tablet properties hardness | : at least 6 kg |
| Decomposition time in water at 20° C. | : maximum 2 minutes |

The thus produced tablets were subsequently overcoated in a known manner with a stomach soluble film. The protective film was formed by application of a suspension which had the following composition and was made in conventional manner:

Composition of 20 kg (about 19.08 liters) of the suspension:

| | |
|---|---|
| Acrylic acid ethylester - methacrylic acid methylester 70 : 30 - Copolymerisate (30% dispersion) | 2.400 kg |
| Titanium dioxide (density 4.05 g. cm³) | 1.600 kg |
| Talc (powdered) | 1.600 kg |
| Dimethyl polysiloxane activated with silica | 0.036 kg |
| = Dimethyl polysiloxane | |
| average molecular weight 24,000 | 0.030 kg |
| activated with silica | 0.006 kg |
| Polyethylene glycol 6000 | 0.600 kg |
| Polyethylene glycol sorbitan monooleate | 0.200 kg |
| Carboxymethyl cellulose - sodium salt | 0.012 kg |
| Purified water | 13.552 kg |
| | 20.00 kg |

Injection solution

For the production of 5,000 ampoules of 2 ml=10 liter of injection solution were required.

300 mg 3β-(3,3 Dimethylacrylic acid ester) of hellebrigenin
1.0 kg 1,2 Propylene glycol
0.5 kg Ethanol
1.0 kg Acetate buffer solution pH 4.5
add to liters of Water.

The 3β-(3,3Dimethylacrylic acid ester) of hellebrigenin was dissolved under nitrogen in the propylene glycol and ethanol at 50° C.
 =Solution 1
After cooling to room temperature 5 liters of water (for injection purposes) were added to solution 1
 =Solution 2
The pH-value of solution 2 was brought to 4.5 by 0.1 N HCl. After that the buffer solution was added
 =Solution 3
Solution 3 was filled up with water for injection purposes to a total volume of 10 liters
 =Injection solution
The injection solution was then filtered under nitrogen and filled into ampoules of 2 ml.
Sterilization: 20 minutes at 120° C.

The resorption quotients of various compounds where $R_3$ in formula (I) is —CHO are given in the following table. The Example No. refers to the example in the present case. This column is left blank for compounds for which there is no working example.

TABLE

| Example | Resorption Quotient | Acyl residue R—CO |
|---|---|---|
| 1 | 38 | $CH_3-CH_2-CH_2-CO-$ |
| 2 | 89 | $(CH_3)_2CH-CO$ |
| 3 | 50 | $(CH_3)_2CH-CH_2-CO$ |
| 4 | 21 | $(CH_3)_3C-CH_2-CO-$ |
| 5 | 0 | $CH_3-CH=CH-CO$ |
| 6A,6B | 90 | $(CH_3)_2C=CH-CO$ |
| 7 | 20 | $CH_3-(CH_2)_6-CO$ |
| 8 | 85 | $CH_3-(CH_2)_8-CO$ |
| — | 17 | hemiphthalic acid residue |
| — | 23 | $CH_3OCO-(CH_2)_8-CO$ |
| — | 0 | $ClCH_2-CO$ |
| — | 0 | $(CH_3O)_2CH-CH_2-N(CH_3)-CH_2-CO-$ |
| — | 22 | $(C_2H_5)_2N-CH_2-CH_2-CO$ |

As can be seen from the above table there does not appear to be any rhyme or reason by which there can be predicted a satisfactory resorption quotient.

The compounds of the invention have a resorption quotient of at least 80%.

It can be seen from the table that the crotonic acid residue has a resorption quotient of 0 while the dimethylacrylic acid residue which differs from it merely by having an additional methyl group in contrast has a resorption quotient of 90%.

Similar unpredictable results are also shown when R is alkyl. Thus with residue of caprylic acid the resorption quotient is only 20% while in the case of the residue of decanoic acid which has merely 2 CH$_2$ groups more, the resorption quotient is 85%. In the case of the isobutyryl residue the resorption residue is 89% while with the unbranched butyric acid residue the resorption quotient is only 38% and in the case of the 3,3-dimethylbutyric acid residue the resorption quotient drops to 21%. Even with the isovaleric acid residue that differs from the isobutyric acid residue by only one —CH$_2$— group, the resorption quotient is only 50%.

What is claimed is:

1. A compound corresponding to the formula

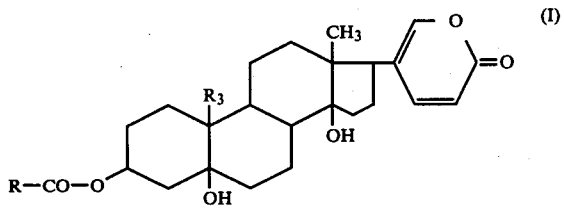

in which R represent 2,2-dimethylethenyl; isopropyl; nonyl; a C$_3$-C$_6$-cycloalkyl radical; a phenyl group substituted by at least one nitro group, or a C$_1$-C$_6$-alkyl group containing a morpholine group attached thereto, said morpholine ring being substituted zero to twice by C$_1$-C$_6$-alkyl group; R$_3$ is —CHO or —CH$_2$OH or a salt of a compound of formula (I) having a basic nitrogen atom with a pharmaceutically acceptable acid.

2. A compound according to claim 1 wherein R$_3$ is —CHO.

3. A compound according to claim 1 wherein R$_3$ is —CH$_2$OH.

4. A compound according to claim 1 wherein R is 2,2-dimethylethenyl; isopropyl; nonyl; cyclopropyl; cyclohexyl or dimethylmorpholino methyl.

5. A compound according to claim 4 wherein R is isopropyl, cyclopropyl, cyclohexyl,

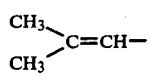

or dimethylmorpholinomethyl and R$_3$ is —CHO.

6. A compound according to claim 4 wherein R is isopropyl or

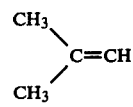

and R$_3$ is —CH$_2$OH.

7. A compound according to claim 4 wherein R is cyclopropyl or cyclohexyl.

8. A medicament containing as an active ingredient a compound of claim 1 together with a pharmaceutical excipient or diluent.

9. A method of combatting the effect of heart insufficiency in a mammal comprising administering to the mammal an effective amount of a compound of claim 1 to increase the power of heart contraction.

10. A method according to claim 9 wherein the compound is administered orally.

11. A method according to claim 10 wherein there is administered orally at least 0.05 mg/kg body weight of the mammal.

12. A method according to claim 9 wherein the compound is administered intravenously.

13. A method according to claim 12 wherein there is administered intravenously at least 0.05 mg/kg body weight of the mammal.

* * * * *